US010561142B2

(12) United States Patent
Parry et al.

(10) Patent No.: US 10,561,142 B2
(45) Date of Patent: *Feb. 18, 2020

(54) DISPERSED LACTAMS

(71) Applicant: Conopco, Inc., Englewood Cliffs, NJ (US)

(72) Inventors: Neil James Parry, Tarporley (GB); Paul Damien Price, Wirral (GB); Sukriti Singh, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/750,895

(22) PCT Filed: Jul. 25, 2016

(86) PCT No.: PCT/EP2016/067616
§ 371 (c)(1),
(2) Date: Feb. 7, 2018

(87) PCT Pub. No.: WO2017/029071
PCT Pub. Date: Feb. 23, 2017

(65) Prior Publication Data
US 2018/0228152 A1   Aug. 16, 2018

(30) Foreign Application Priority Data
Aug. 20, 2015 (EP) .................... 15181830

(51) Int. Cl.
*A01N 43/36* (2006.01)
*A01N 25/10* (2006.01)

(52) U.S. Cl.
CPC ............ *A01N 43/36* (2013.01); *A01N 25/10* (2013.01)

(58) Field of Classification Search
CPC ................ A01N 43/36; A01N 25/10
See application file for complete search history.

(56) References Cited

U.S. PATENT DOCUMENTS

| 5,955,419 A | 9/1999 | Barket, Jr. et al. |
| 8,641,948 B2 * | 2/2014 | Ghogh ................. A61K 9/1641 |
| | | 264/176.1 |
| 9,586,901 B2 | 3/2017 | Kumar et al. |
| 9,930,888 B2 | 4/2018 | Parry et al. |
| 2011/0059144 A1 | 3/2011 | Fletcher et al. |
| 2014/0294925 A1 | 10/2014 | Yin |
| 2015/0351393 A1 * | 12/2015 | Parry ................... A61Q 17/005 |
| | | 424/65 |

FOREIGN PATENT DOCUMENTS

| WO | WO2006085089 | 8/2006 |
| WO | WO2007085042 | 8/2007 |
| WO | WO2010069742 | 6/2010 |
| WO | WO2014118240 | 8/2014 |

OTHER PUBLICATIONS

Guedes et al. (PharmSciTech 12(1); 401-410, 2011).*
Chadha et al. (J. Scitific and Industrial Reseasrch 65;459-469 (2006)).*
Kim et al. (J. Pharmaceutical Investigation 41(3) 125-142 (2011)).*
Carla S.M. Pereira et al., Ethyl lactate as a solvent: properties, applications and production processes—a review, Green Chemistry, 2011, pp. 2658-2671; XP055235519, vol. 13, No. 10.
IPRP in PCTEP2016069072, Aug. 2, 2017.
IPRP2 in PCTEP2016068585, Nov. 2, 2017.
IPRP2 in PCTEP2016068625, Sep. 6, 2017.
Mary E. Davey et al., Rhamnolipid Surfactant production Affects Biofilm Architecture in Pseudomonas aeruginosa PAO1, Journal of Bacteriology, 2003, pp. 1027-1036, vol. 185, No. 3, American Society for Microbiology.
Ondrej Krenk et al., Methodology for Synthesis of Enantiopure 3,5-Disubstituted Pyrrol-2-ones, European Journal of Organic Chemistry, 2015, pp. 5414-5423; XP002752111.
Search Report & Written Opinion in EP15181849, dated Feb. 23, 2016.
Search Report & Written Opinion in PCTEP2016069072, dated Sep. 14, 2016.
Search Report and Written Opinion in PCTEP2016067613, dated Sep. 21, 2016.
Report and Written Opinion in PCTEP2016067616, dated Sep. 12, 2016.
Report and Written Opinion in PCTEP2016068008, dated Sep. 12, 2016.
Report and Written Opinion in PCTEP2016068010, dated Sep. 12, 2016.
Report and Written Opinion in PCTEP2016068287, dated Oct. 26, 2016.
Report and Written Opinion in PCTEP2016068585, dated Oct. 4, 2016.

(Continued)

Primary Examiner — Shirley V Gembeh
(74) Attorney, Agent, or Firm — Foley & Lardner LLP

(57) ABSTRACT

Lactams in solid dispersions suitable for use in compositions. The compositions may be useful as antimicrobial, anti-biofilm and bacteriostatic compositions. Methods of making lactams in solid dispersions. Methods of making compositions using lactams in solid dispersions.

14 Claims, 1 Drawing Sheet

(56) References Cited

OTHER PUBLICATIONS

Report and Written Opinion in PCTEP2016068625, dated Sep. 9, 2016.
Report in EP15181842, Dec. 10, 2015.
Report in EP15181846, Dec. 11, 2015.
Report in EP15181847, Dec. 17, 2015.
Report in EP15181851, Dec. 11, 2015.
Report in EP15181856, Dec. 14, 2015.
Search Report in EP15181858, dated Dec. 11, 2015.
Von R. Scheffold Und P. Dubs, Synthese von Azaprotoanemoninen, Helvetica Chimica Acta, 1967, pp. 798-808; XP55249911.
Written Opinin in EP15181856, dated Dec. 14, 2015.
Written Opinion 2 in PCTEP2016067613, dated Jul. 11, 2017.
Written Opinion in EP15181842, dated Dec. 10, 2015.
Written Opinion in EP15181846, dated Dec. 11, 2015.
Written Opinion in EP15181847, dated Dec. 17, 2015.
Written Opinion in EP15181851, dated Dec. 11, 2015.
Written Opinion in EP15181858, dated Dec. 11, 2015.
Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.

\* cited by examiner

DISPERSED LACTAMS

This application claims priority from EP 15181830.9 filed 20 Aug. 2015 which is incorporated by reference for all purposes.

The present invention relates to lactams in solid dispersions. The lactams in solid dispersions are suitable for use compositions, for example, in antimicrobial, anti-biofilm and bacteriostatic compositions. The invention further relates to a method of forming a lactam in solid dispersion.

WO 2007/085042 and WO 2004/016588 disclose lactams for antimicrobial benefit and steps towards their synthesis. WO2014/118240 discloses antimicrobial compositions comprising a lactam and a hydrotope.

However, use of these lactams is limited by solubility, particularly in aqueous compositions, but also in non-aqueous compositions.

The present invention relates to lactams in solid dispersions. The use of solid dispersions of the lactams permits greater flexibility of formulation as solubility is improved and/or the use of a solid dispersion may improve stability of the lactam in the formulation.

More specifically, the present invention relates to dispersions comprising lactams as described in WO 2007/085042 and WO 2004/016588, the contents of which, and in particular the lactam structures explicitly drawn out therein, are incorporated by reference.

For example, in a first aspect, the present invention relates to a lactam in as solid dispersion, wherein the lactam is lactam of formula (I) or (II):

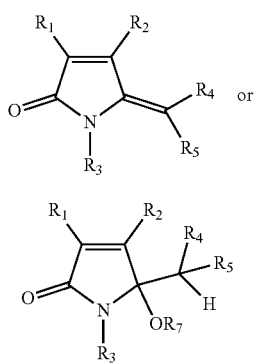

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl and $C(O)CR_6=CH2$;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and $C(O)CR_6=CH2$; and Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

Accordingly, in a first aspect, the present invention may provide a lactam in a solid dispersion, wherein the lactam is a lactam of Formula Ia or Formula IIa:

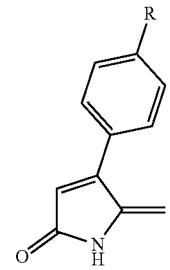

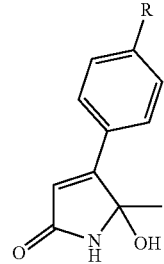

wherein R is H, halogen (preferably, F, Cl, or Br), or $C_{1-4}$alkyl (preferably methyl).

The lactam in a solid dispersion may also be termed a solid dispersion comprising a lactam, or a solid composition comprising a dispersed lactam.

In some embodiments, the lactam is a lactam of formula Ia. In some embodiments, the lactam is a lactam of formula IIa.

Importantly, lactams of formula Ia have been found to be unstable in high pH7 conditions (high pH refers to a pH of at least 7). Use of a solid dispersion improves stability in these conditions, permitting the lactams to be used in a wider variety of compositions.

Preferred lactams may include:

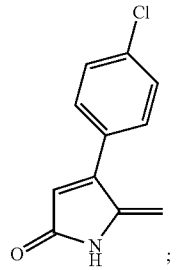

(Ref. 488)

4-(4-chlorophenyl)-5-methylene-pyrrol-2-one (Ref. 491)

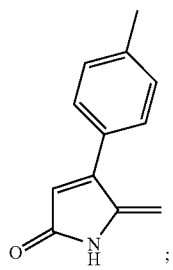

5-methylene-4-(p-tolyl)pyrrol-2-one (Ref. 131)

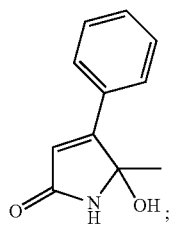

4-phenyl-5-hydroxy-5-methyl-1H-pyrrol-2-one (Ref. 258)

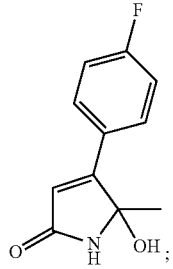

4-(4-fluorophenyl)-5-hydroxy-5-methyl-1H-pyrrol-2-one (Ref. 316)

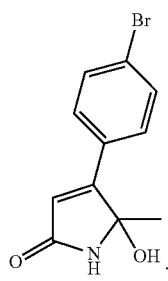

4-(4-bromophenyl)-5-hydroxy-5-methyl-1H-pyrrol-2-one

Suitably, the solid dispersion is comprises a polymer and a lactam. Suitably, the polymer is completely water soluble.

Any suitable polymer may be used, and suitable polymers are known in the art. Examples may include hydroxypropylmethyl-cellulose (HPMC), polyvinylpyrrolidone (PVP), partially hydrolyzed polyvinyl alcohol (PVA), pullulan, and polytheylene glycol (PEG). In some cases, the polymer of the solid dispersion is polyvinylpyrrolidone (PVP) or polyethyleneglycol (PEG). Suitably, the PEG may have a molecular weight of 1.5 k, 10 k or 20 k. It will be appreciate that mixtures of polymers may be used.

In some cases the amount of lactam in the solid dispersion is around 1% wt. of the solid dispersion. Of course, it may be higher, for example, up to 3% wt., up to 5% wt., up to 7% wt., or even up to 10% wt. For example, the solid dispersion may comprise 0.01 to 10% wt. lactam.

The lactams in solid dispersions are suitable for use in making compositions. The composition may be, without limitation, any of a personal care composition, a homecare composition, a pharmaceutical composition, or an industrial composition such as an anti-biofilm coating or paint, for example, for use in maritime environments. The composition may also be an agricultural chemical. The compositions may be suitable for use as antimicrobial, anti-biofilm and bacteriostatic compositions. Non-limiting examples of such compositions are provided herein. The compositions may also be used as additive compositions; in other words, the composition may be combined with further ingredients such as excipients to form a composition as described above. The lactam may be a lactam of Formula I or Formula II.

Accordingly, in a second aspect the present invention may provide a method of making a composition comprising a lactam, the method comprising combining a lactam in a solid dispersion with a solvent or excipient, wherein the lactam is a lactam of Formula Ia or IIa (wherein R is as defined herein). Suitably, the composition is an antimicrobial composition.

Preferred lactams may be as described for the first aspect.

In a third aspect, the present invention provides a composition obtainable by the method of the second aspect.

Advantageously, the composition may be a composition of pH ≥7, for example ≥8, for example ≥9, for example ≥10, for example ≥11.

Preferably the composition contains 0.000001 to 50% wt. lactam, more preferably 0.001 to 50% wt. even more preferably 0.01 to 5% wt., most preferably 0.01 to 2%.

In a fourth aspect, the present invention relates to method of forming a lactam in a solid dispersion, the method comprising dissolution and removal of a solvent in vacuo. The lactam may be a lactam of Formula I or Formula II, and the options and preferences described below may apply.

Accordingly, in a fourth aspect the present invention may provide a method of forming lactam in a solid dispersion, wherein the lactam is a lactam of Formula Ia or IIb (wherein R is as described herein), the method comprising:

(a) combining said lactam with a polymer in a solvent; then (b) heating said solvent until dissolution occurs; then (c) cooling the solution to room temperature; then (d) removing the solvent to obtain a dry residue.

Suitably, the dry residue may be ground to give a fine powder. Use of the solid dispersion as a fine powder may improve ease of use in formulations, for example by increasing the rate of dissolution.

The solvent may be acetonitrile.

The polymer of the solid dispersion may be polyvinylpyrrolidone (PVP) or polyethyleneglycol (PEG). Suitably, the PEG may have a molecular weight of 1.5 k, 10 k or 20 k.

It will be appreciated that options and preferences described with respect to the first aspect apply equally where possible to the other aspects, and vice versa.

FIGURES

FIG. 1 shows samples of (from left to right) PVP alone, Lactam/PVP dispersion, lactam alone, Lactam/PVP physical mixture.

DESCRIPTION

Lactams may be obtained using methods as described in WO 2007/085042 and WO 2004/016588, which are herein incorporated by reference in their entirety.

Solid Dispersion

Solid dispersion, as used herein, refers to a solid product containing at least two components: a hydrophilic matrix and a hydrophobic active ingredient. The matrix can be either crystalline or amorphous and the active can be dispersed molecularly, in amorphous particles, or in crystalline particles. Solid dispersions confer enhanced aqueous solubility to the hydrophobic active ingredients.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

EXAMPLES

Solid dispersions of lactams 4-(4-bromophenyl)-5-hydroxy-5-methyl-1H-pyrrol-2-one and 4-(4-chlorophenyl)-5-methylene-pyrrol-2-one in PEG (1.5 k, 10 k or 20 k molecular weight) or polyvinylpyrrolidone (PVP, 40 k molecular weight) were prepared according to the following method:

Lactam and polymer (PVP or PEG) were combined in the required ratio, suspended in acetonitrile and heated to bring about dissolution. Following this, the solution was cooled to room temperature and the solvent removed in vacuo to furnish the desired solid dispersion. The material was dried under vacuum for an extended time to ensure all residual solvent was removed and ground to give a fine powder.

The inventor(s) have shown that solid dispersion of lactam in PVP confers enhanced aqueous solubility to the lactam. As can be seen in the photo below, PVP alone and a solid dispersion of 1% lactam in PVP both dissolve rapidly in water to give a clear solution. An equivalent amount of lactam to that contained in the solid dispersion does not dissolve, while in a mixture of lactam and PVP added separately to water, only the PVP dissolves and the lactam does not. Note that this example is a proof of concept, and the lactam used was 4-(4-fluorophenyl)-5-methylene-pyrrol-2-one.

These results show that the rate of dissolution of lactams in water can be increased through the production of a solid dispersion in PVP or PEG. Such solid dispersions dissolve rapidly to give clear solutions.

It will be appreciated that, except where expressly provided otherwise, all preferences are combinable.

The invention claimed is:

1. A lactam in a solid dispersion, wherein the lactam is a lactam of Formula Ia or Formula IIa:

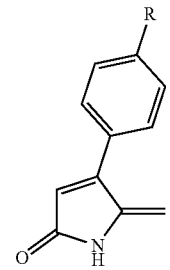

Ia

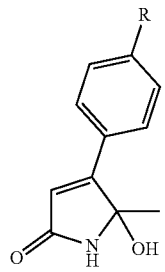

wherein:
R is H, halogen, or $C_{1-4}$alkyl;
the solid dispersion comprises polyvinylpyrrolidone (PVP); and
the solid dispersion comprises 0.01 and 10% wt. lactam.

2. The lactam in a solid dispersion of claim 1, wherein R is H, F, Cl, Br, or Me.

3. The lactam in a solid dispersion of claim 1, wherein the lactam is selected from:

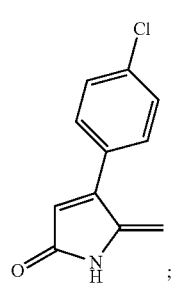

(Ref. 488)

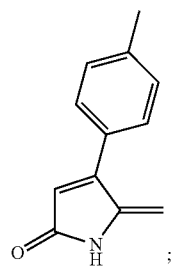

(Ref. 491)

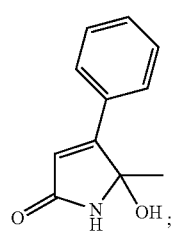

(Ref. 131)

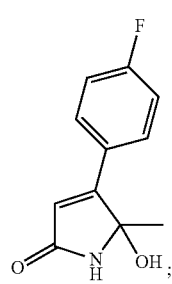

(Ref. 258)

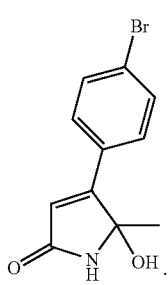

(Ref. 316)

4. The composition of claim 1, wherein the PVP has a molecular weight of 40 k.

5. A method of making a composition comprising a lactam, the method comprising combining a lactam in a solid dispersion according to claim 1 with a solvent or excipient.

6. A method of forming lactam in a solid dispersion, wherein the lactam is a lactam of Formula Ia or Formula IIa:

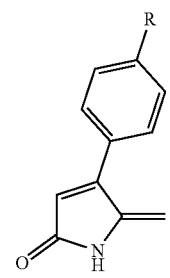

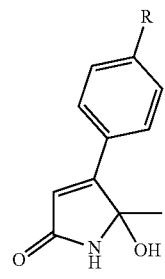

wherein R is H, halogen, or $C_{1-4}$alkyl,
the method comprising:
(a) combining said lactam with a polymer in a solvent, wherein the polymer is selected from polyvinylpyrrolidone (PVP) or polyethyleneglycol (PEG); then
(b) heating said solvent until dissolution occurs; then
(c) cooling the solution to room temperature; then
(d) removing the solvent to obtain a dry residue comprising 0.01 to 10% wt. of said lactam;
optionally wherein the method further comprises:
(e) grinding the dry residue.

7. A lactam in a solid dispersion, wherein the lactam is a lactam of Formula Ia or Formula IIa:

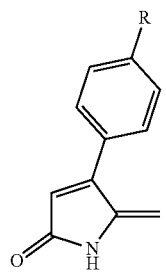

Ia

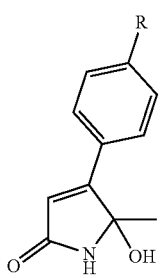

IIa wherein:

R is H, halogen, or $C_{1-4}$alkyl;

the solid dispersion comprises 0.01 to 10% wt. lactam; and the solid dispersion comprises polyethyleneglycol (PEG)

the solid dispersion comprises 0.01 and 10% wt. lactam.

8. The lactam in a solid dispersion of claim 7, wherein R is H, F, Cl, Br, or Me.

9. The lactam in a solid dispersion of claim 7, wherein the lactam is selected from:

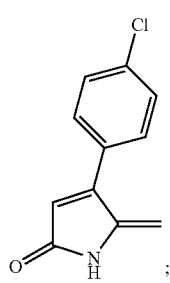
(Ref. 488)

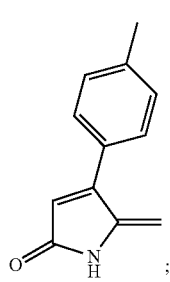
(Ref. 491)

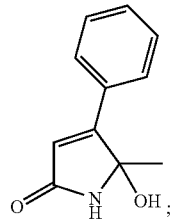
(Ref. 131)

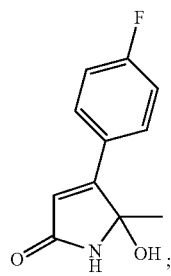
(Ref. 258)

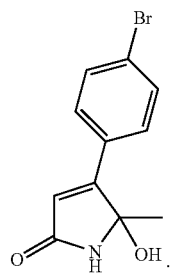
(Ref. 316)

10. The lactam in a solid dispersion of claim 7, wherein the polyethyleneglycol may comprise a molecular weight of 1.5 k to 20 k.

11. A composition comprising the solid dispersion of claim 7 dissolved in water.

12. The composition of claim 11, wherein the composition has a pH ≥7.

13. A composition comprising a lactam, polyvinylpyrrolidone (PVP), and water, wherein the lactam is a lactam of Formula Ia or Formula IIa:

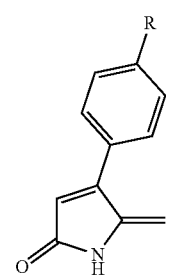
Ia

-continued
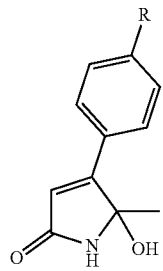
IIa
wherein R is H, halogen, or $C_{1-4}$alkyl.
14. The composition of claim 13, wherein the composition has a pH $\geq 7$.
* * * * *